United States Patent
Furman (10) Patent No.: US 8,442,606 B2
(45) Date of Patent: May 14, 2013

(54) OPTICAL SENSOR APPARATUS AND METHOD OF USING SAME

(75) Inventor: Dan Gur Furman, Gedera (IL)

(73) Assignee: Cardio Art Technologies Ltd., Or Yehuda (IL)

( * ) Notice: Subject to any disclaimer, the term of this patent is extended or adjusted under 35 U.S.C. 154(b) by 1310 days.

(21) Appl. No.: 12/119,315

(22) Filed: May 12, 2008

(65) Prior Publication Data

US 2008/0275321 A1    Nov. 6, 2008

Related U.S. Application Data (63) Continuation-in-part of application No. PCT/IL2006/001416, filed on Dec. 10, 2006.

(60) Provisional application No. 60/748,218, filed on May 12, 2008.

(30) Foreign Application Priority Data

Aug. 30, 2007    (IL) .......................................... 185609

(51) Int. Cl.
    *A61B 5/1455*    (2006.01)
(52) U.S. Cl.
    USPC .......................................... 600/323; 600/340
(58) Field of Classification Search .................. 600/310, 600/322, 323, 340
    See application file for complete search history.

(56) References Cited

U.S. PATENT DOCUMENTS

| | | | |
|---|---|---|---|
| 4,770,177 | A | 9/1988 | Schroeppel |
| 5,113,869 | A | 5/1992 | Nappholz et al. |
| 5,174,295 | A | 12/1992 | Christian et al. |
| 5,218,962 | A | 6/1993 | Mannheimer et al. |
| 5,309,916 | A | 5/1994 | Hatschek |
| 5,409,009 | A | 4/1995 | Olson |
| 5,464,434 | A | 11/1995 | Alt |
| 5,488,953 | A | 2/1996 | Vilkomerson |
| 5,544,649 | A | 8/1996 | David et al. |
| 5,558,092 | A | 9/1996 | Unger et al. |
| 5,606,972 | A | 3/1997 | Routh |
| 5,713,939 | A | 2/1998 | Nedungadi et al. |
| 5,772,589 | A | 6/1998 | Bernreuter |
| 5,817,009 | A | 10/1998 | Rosenheimer et al. |
| 5,833,603 | A | 11/1998 | Kovacs et al. |
| 5,995,208 | A | 11/1999 | Sarge et al. |
| 6,053,873 | A | 4/2000 | Govari et al. |
| 6,176,832 | B1 | 1/2001 | Habu et al. |
| 6,206,835 | B1 | 3/2001 | Spillman, Jr. et al. |
| 6,231,516 | B1 | 5/2001 | Keilman et al. |

(Continued)

FOREIGN PATENT DOCUMENTS

| | | |
|---|---|---|
| WO | WO 92/20273 | 11/1992 |
| WO | WO 93/17621 | 9/1993 |

(Continued)

OTHER PUBLICATIONS

International Preliminary Report on Patentability on PCT Application No. PCT/IL2006/001416; issued Mar. 10, 2009; 7 pages; International Bureau of WIPO, Geneva, Switzerland.

(Continued)

*Primary Examiner* — Eric Winakur
(74) *Attorney, Agent, or Firm* — Faegre Baker Daniels LLP (57) ABSTRACT

An apparatus for, and method of, sensing characteristics of a vessel and a fluid conveyed therein.

38 Claims, 9 Drawing Sheets

U.S. PATENT DOCUMENTS

| | | | |
|---|---|---|---|
| 6,261,233 B1 | 7/2001 | Kantorovich | |
| 6,277,078 B1 | 8/2001 | Porat et al. | |
| 6,398,731 B1 | 6/2002 | Mumm et al. | |
| 6,475,153 B1 | 11/2002 | Khair et al. | |
| 6,485,418 B2 | 11/2002 | Yasushi et al. | |
| 6,609,023 B1 | 8/2003 | Fischell et al. | |
| 6,622,322 B1 | 9/2003 | Caveney | |
| 6,929,610 B2 | 8/2005 | Forstner | |
| 7,004,907 B2 | 2/2006 | Banet et al. | |
| 7,125,383 B2 | 10/2006 | Hoctor et al. | |
| 7,127,300 B2 | 10/2006 | Mazar et al. | |
| 7,179,228 B2 | 2/2007 | Banet | |
| 7,238,159 B2 | 7/2007 | Banet et al. | |
| 7,267,649 B2 | 9/2007 | Zdeblick et al. | |
| 7,272,428 B2 | 9/2007 | Hopman et al. | |
| 7,308,292 B2 | 12/2007 | Colvin et al. | |
| 7,396,330 B2 | 7/2008 | Banet et al. | |
| 2002/0010390 A1 | 1/2002 | Guice et al. | |
| 2002/0095092 A1 | 7/2002 | Kondo et al. | |
| 2003/0097068 A1 | 5/2003 | Hossack et al. | |
| 2003/0139778 A1 | 7/2003 | Fischell et al. | |
| 2004/0106953 A1 | 6/2004 | Yomtov et al. | |
| 2004/0167416 A1 | 8/2004 | Lee | |
| 2004/0236223 A1 | 11/2004 | Barnes et al. | |
| 2005/0096557 A1 | 5/2005 | Vosburgh et al. | |
| 2005/0216199 A1 | 9/2005 | Banet | |
| 2005/0228299 A1 | 10/2005 | Banet | |
| 2005/0228300 A1 | 10/2005 | Jaime et al. | |
| 2005/0245831 A1 | 11/2005 | Banet | |
| 2005/0245882 A1 | 11/2005 | Elkins et al. | |
| 2005/0261594 A1 | 11/2005 | Banet | |
| 2006/0009697 A1 | 1/2006 | Banet et al. | |
| 2006/0009698 A1 | 1/2006 | Banet et al. | |
| 2006/0100530 A1 | 5/2006 | Kliot et al. | |
| 2006/0129038 A1 | 6/2006 | Zelenchuk et al. | |
| 2006/0224053 A1 | 10/2006 | Black et al. | |
| 2006/0253007 A1 | 11/2006 | Cheng et al. | |
| 2007/0088214 A1 | 4/2007 | Shuros et al. | |
| 2007/0093702 A1 | 4/2007 | Yu et al. | |
| 2007/0142715 A1 | 6/2007 | Banet et al. | |
| 2007/0185393 A1 | 8/2007 | Zhou et al. | |
| 2007/0244398 A1 | 10/2007 | Lo et al. | |
| 2007/0265533 A1 | 11/2007 | Tran | |
| 2007/0276261 A1 | 11/2007 | Banet et al. | |
| 2007/0276632 A1 | 11/2007 | Banet et al. | |
| 2007/0299318 A1 | 12/2007 | Chen et al. | |
| 2008/0027323 A1 | 1/2008 | Freiburger | |
| 2008/0077026 A1 | 3/2008 | Banet et al. | |
| 2008/0082004 A1 | 4/2008 | Banet et al. | |
| 2008/0114220 A1 | 5/2008 | Banet et al. | |
| 2008/0195043 A1 | 8/2008 | Swach et al. | |
| 2008/0221399 A1 | 9/2008 | Zhou et al. | |
| 2008/0221461 A1 | 9/2008 | Zhou et al. | |

FOREIGN PATENT DOCUMENTS

| | | |
|---|---|---|
| WO | WO01/85014 | 11/2001 |
| WO | WO03/015838 | 2/2003 |
| WO | WO 2006/113748 | 10/2006 |
| WO | WO 2007/035934 | 3/2007 |
| WO | WO 2007/0066343 | 6/2007 |
| WO | WO 2007/122375 | 11/2007 |

OTHER PUBLICATIONS

Office Action dated Dec. 22, 2010, in commonly owned U.S. Appl. No. 12/119,339.

European Patent Office, International Search Report for related PCT application PCT/IB2009/006078, Nov. 5, 2009, Rijswijk, Netherlands.

Chemla et al., Blood flow acceleration in the carotid and brachial arteries of healthy volunteers: respective contributions of cardiac performance and local resistance, 1996, Fundam Clin Pharmacol, 10, pp. 393-399.

Tahmasebpour et al., Sonographic Examination of the Carotid Arteries, 2005, RadioGraphics, 25, pp. 1561-1575.

Office Action dated Oct. 7, 2011, in commonly owned U.S. Appl. No. 12/119,339, 20 pgs.

Office Action dated Dec. 21, 2011, in commonly owned U.S. Appl. No. 12/206,885, 14 pgs.

Office Action dated Dec. 15, 2011, in commonly owned U.S. Appl. No. 12/119,325, 12 pgs.

Office Action dated Dec. 13, 2011, in commonly owned U.S. Appl. No. 12/119,462, 9 pgs.

OPTICAL SENSOR APPARATUS AND METHOD OF USING SAME

CROSS-REFERENCE TO RELATED APPLICATIONS

The present application claims priority to and is a continuation-in-part of Israel Patent Application No. 185609 filed Aug. 30, 2007, titled "MULTI FUNCTION SENSSOR," and International Patent Application No. PCT/IL2006/001416 filed Dec. 10, 2006, titled "IMPLANTABLE BIOSENSING DEVICE AND HEALTH MONITORING SYSTEM AND METHOD INCLUDING SAME," which claims the benefit of U.S. Provisional Patent Application Ser. No. 60/748,218 filed Dec. 8, 2005, titled "WIRELESS INTEGRATED TRANSMITTER AND SENSOR," the disclosures of which are expressly incorporated by reference herein.

The present application is related to U.S. Utility Patent Application Ser. No. 12/119,339 titled "DOPPLER MOTION SENSOR APPARATUS AND METHOD OF USING SAME," filed on even date herewith, U.S. Utility Patent Application Serial No. 12/119,325 titled "INTEGRATED HEART MONITORING DEVICE AND METHOD OF USING SAME" filed on even date herewith, and U.S. Utility Patent Application Serial No. 12/119,462 titled "METHOD AND SYSTEM FOR MONITORING A HEALTH CONDITION" filed on even date herewith, the entire disclosure of each application being expressly incorporated by reference herein.

FIELD OF THE INVENTION

The present invention relates to sensing devices and, more specifically, to sensing devices for locating and/or measuring objects.

BACKGROUND AND SUMMARY OF THE INVENTION

For medical reasons, in vivo parameters of a patient may need to be monitored over a period of time. Heart arrhythmias are changes in the normal sequence of electrical impulses that cause the heart to pump blood through the body. Continuous monitoring may be required to detect arrhythmias because abnormal heart impulse changes might only occur sporadically. With continuous monitoring, medical personnel can characterize cardiac conditions and establish a proper course of treatment.

One prior art device that measures heart rate is the "Reveal" monitor by Medtronic (Minneapolis, Minn., USA). This device comprises an implantable heart monitor used, for example, in determining if syncope (fainting) in a patient is related to a heart rhythm problem. The Reveal monitor continuously monitors the rate and rhythm of the heart for up to 14 months. After waking from a fainting episode, the patient places a recording device external to the skin over the implanted Reveal monitor and presses a button to transfer data from the monitor to the recording device. The recording device is provided to a physician who analyzes the information stored therein to determine whether abnormal heart rhythm has been recorded. The use of the recording device is neither automatic nor autonomic, and therefore requires either the patient to be conscious or another person's intervention to transfer the information from the monitor to the recording device.

Another known type of implantable monitoring device is a transponder-type device, in which a transponder is implanted in a patient and is subsequently accessed with a hand-held electromagnetic reader in a non-invasive manner. An example of the latter type of device is described in U.S. Pat. No. 5,833,603.

A sensing device and a method of acquiring signals and computing measurements according to one embodiment of the invention are disclosed herein. The sensing device comprises a sensor assembly and a computing device. The sensor assembly includes a plurality of emitters and a plurality of detectors for generating a plurality of signals. The emitters and detectors face one side of a vessel. A computing device operates the plurality of emitters and detectors and processes the plurality of signals to obtain measurement values. The sensor assembly and the computing device are enclosed in a housing.

One embodiment of a method according to the invention includes the steps of providing a sensor device such as the one described in the paragraph above, operating the plurality of emitters and detectors to obtain a plurality of signals, processing the signals to obtain measurement values, and analyzing the measurement values to obtain parameter values indicative of a characteristic of at least one of the vessel and the fluid.

Another embodiment according to the invention discloses a device for optically measuring a characteristic of at least one of a blood vessel and blood flowing through the blood vessel. The device includes a housing, a sensor assembly, and a computing device. The sensor assembly is mounted to the housing and includes a plurality of emitters for emitting photons through a first side of the housing and a plurality of detectors for receiving at least a portion of the emitted photons through the first side of the housing. Each emitter is operationally paired with a separate detector and oriented such that a beam of photons emitted from the emitter that impinges upon a vessel adjacent the sensor assembly will partially reflect toward the paired detector, each detector being configured to produce a signal representing the emitted photons received by the detector. The computing device is configured to activate the plurality of emitters and interpret the signals from the detectors to determine the characteristic.

The features of this invention, and the manner of attaining them, will become more apparent and the invention itself will be better understood by reference to the following description of embodiments of the invention taken in conjunction with the accompanying drawings.

Corresponding reference characters indicate corresponding parts throughout the several views. Although the drawings represent embodiments of the present invention, the drawings are not necessarily to scale and certain features may be exaggerated in order to better illustrate and explain the present invention. The exemplifications set out herein illustrate embodiments of the invention in several forms and such exemplification is not to be construed as limiting the scope of the invention in any manner.

DETAILED DESCRIPTION OF EMBODIMENTS OF THE INVENTION

The embodiments discussed below are not intended to be exhaustive or limit the invention to the precise forms disclosed in the following detailed description. Rather, the embodiments are chosen and described so that others skilled in the art may utilize their teachings.

Figure 1A:
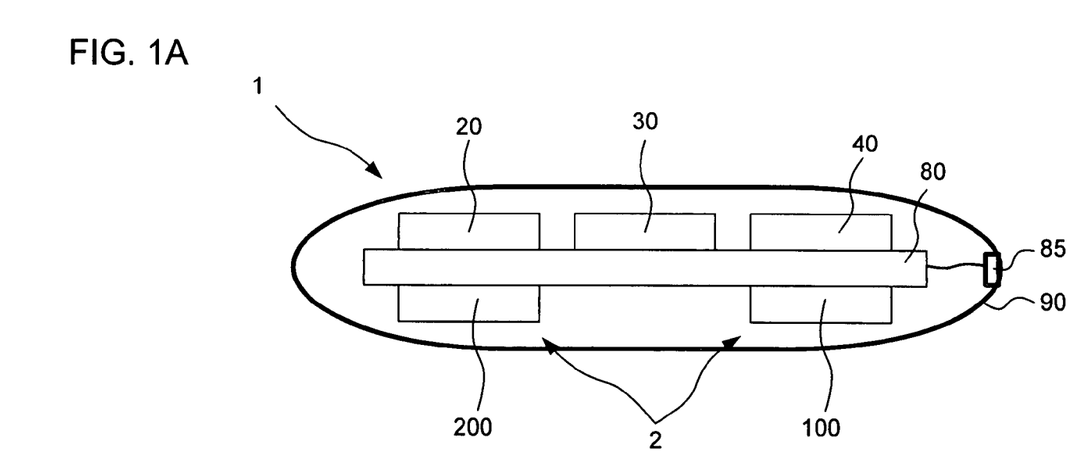
FIG. 1A is a schematic side view of a sensing device according to one embodiment of the invention.

FIG. 1A illustrates a sensing device 1 according to one embodiment of the invention. Sensing device 1 generally includes a plurality of components including a sensor assembly 2, a computing device 20, a communication device 30, and an energy storage device 40, each of the components mounted on a board 80 and being in electronic communication with computing device 20. The components are enclosed in a housing 90. Sensor assembly 2 includes an emitter array 100 having a plurality of emitters and a detector array 200 having a plurality of detectors.

In one embodiment according to the invention, sensing device 1 is adapted to determine a physiological condition of a patient. By "patient" it is meant a person or animal whose physiological condition is measured by sensing device 1. Although the invention disclosed herein is described in the medical context, the teachings disclosed herein are equally applicable in other contexts where compact data acquisition assemblies are desirable to perform measurements over time. For example, sensor assemblies according to the invention may be desirable in submersed or difficult to reach applications, in dangerous environments, in applications having weight and size restrictions, in field research activities, and so on.

Figure 1B:
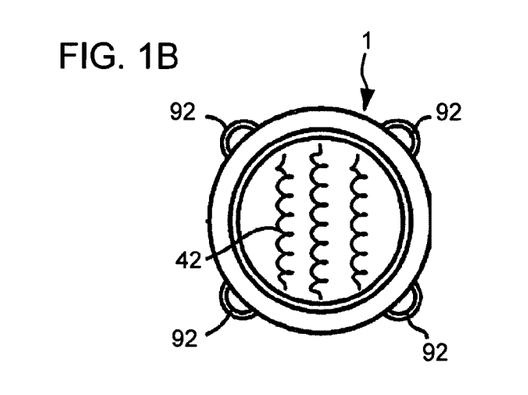
FIG. 1B is an outwardly-facing view of the sensing device of FIG. 1.
Figure 1C:
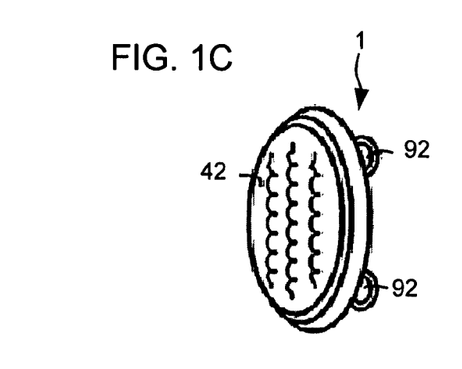
FIG. 1C is a perspective view of the sensing device of FIG. 1.

In one embodiment according to the invention, sensing device 1 is implanted subcutaneously in the patient's body. It should be understood, however, that sensing device 1 may be implanted at different locations using various implantation techniques. For example, sensing device 1 may be implanted within the chest cavity beneath the rib cage. Housing 90 may be formed in the shape of a circular or oval disc, with dimensions roughly the same as two stacked quarter dollar coins. Of course, housing 90 may be configured in a variety of other shapes, depending upon the application. It may include four outwardly projecting loops 92, shown in FIGS. 1B and 1C, for receiving sutures in order to fix the assembly subcutaneously within the patient's body. More or fewer loops 92 may be provided depending upon the shape of housing 90. When so fixed, sensor assembly 2 is positioned facing inwardly while an energy coupler, which is described with particularity below, faces outwardly.

In another embodiment, sensing device 1 is positioned externally to the patient's body. A support member is provided to support sensing device 1 externally to the body. The support member may be permanently or temporarily coupled to sensing device 1. In one embodiment, the support member comprises an adhesive layer for adhesively coupling the support member to the patient's body. In another embodiment, the support member comprises a belt, which may be elastic, for holding sensing device 1 against the patient's body.

Sensing device 1 may be implanted subcutaneously or positioned on the patient with the aid of an external mapping system such as an ultrasound machine. Proper placement ensures that a vessel of interest is located within the sensing range of sensing device 1. Where the vessel of interest is the aorta, sensing device 1 may be positioned on the chest or back of the patient in a location that reduces interference by the ribs of the measurements acquired in the manner described herein.

In one embodiment according to the invention, sensing device 1 has a communication port for connecting to, and exchanging information with, other devices. Connector 85 is shown. The operation of connector 85, which is connected to other components of sensing device 1 through board 80, is described in more detail further below with reference to FIGS. 6A and 6B.

1. Vessel Detector

In one embodiment according to the invention, sensing device 1 senses parameters of the patient's blood conveyed in a vessel such as a vein or an artery. In an exemplary embodiment, sensing device 1 emits beams of electromagnetic energy in the infrared (IR) range of the electromagnetic spectrum and detects IR signals reflected from blood circulating in the vessel. It should be understood, however, that other types of electromagnetic energy may be employed consist with the teachings of the invention. Sensing device 1 may emit IR beams at one or more frequencies selected for their ability to pass through the patient's body with minimal interference or absorption by the body and to reflect from specific blood components selected for their ability to convey the desired blood parameters values. In the exemplary embodiment, sensing device 1 emits infrared beams selected to reflect from haemoglobin, which is the iron-containing oxygen-transport metalloprotein in red blood cells.

Photocell arrays may be utilized to emit and detect the IR beams. As disclosed in detail below, each array is displayed as having sixteen photocells arranged in a grid of four rows with four cells each. Under certain operating conditions described below, all of the photocells in emitter array 100 emit beams simultaneously, while under other operating conditions each photocell emits a beam at a selected time to obtain specific information and/or to conserve energy. In yet another embodiment, photocells are dispersed over the surface of the sensing device in any manner, including in arrangements where emitters and detectors are interspersed and/or dispersed in alternating rows or columns of emitters and detectors.

Figure 2:
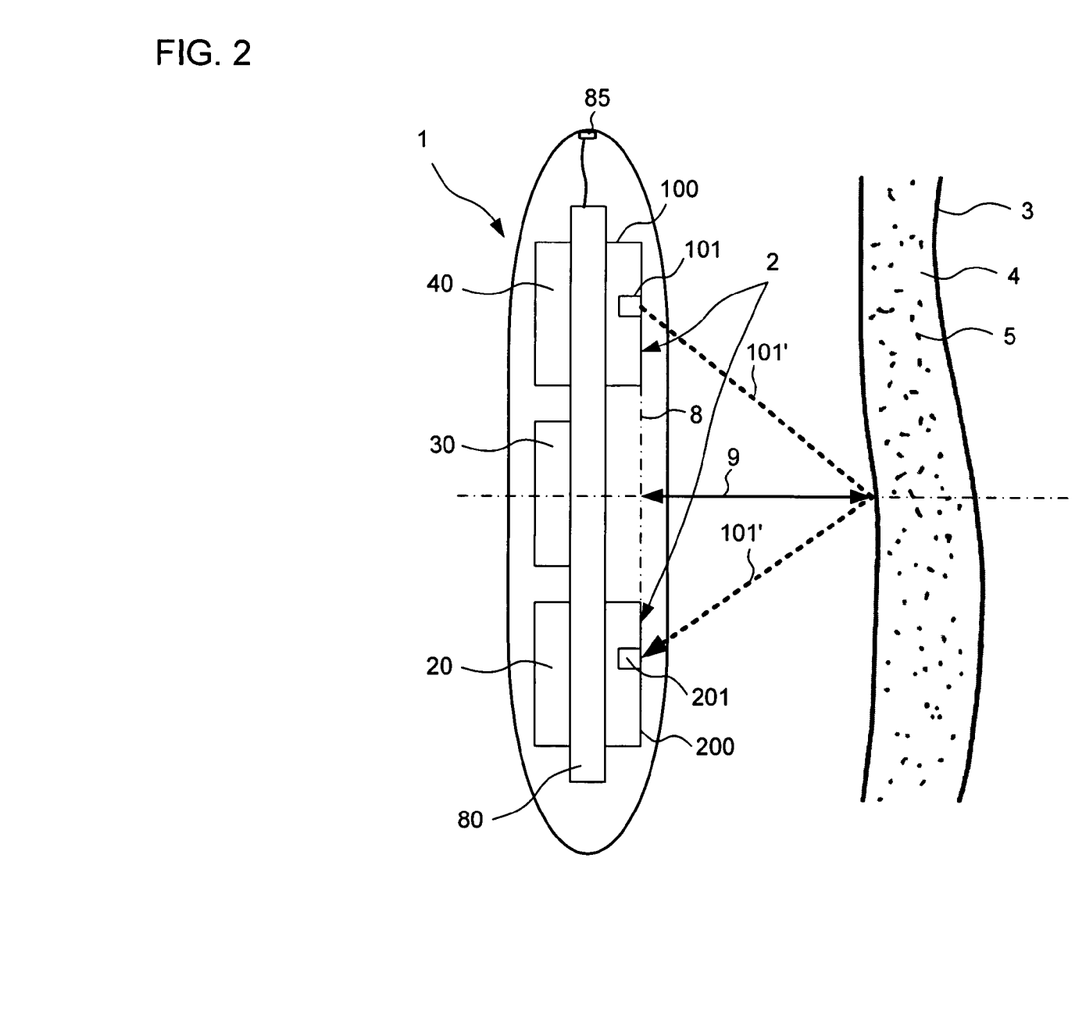
FIG. 2 is a schematic side view of the sensing device of FIG. 1 and a vessel.

FIG. 2 illustrates the relationship between a vessel 3 conveying blood 4 having haemoglobin in red blood cells 5 and a pair of photocells, emitter 101 and detector 201, or sensor assembly 2. Sensor assembly 2 may be selected from the 8572 family of optical sensors manufactured by Motorola. Emitter 101 emits a beam of photons including photon 101'. As described in further detail below with reference to FIG. 3, a portion of the photons in the beam pass through vessel 3 and a portion are reflected as a reflected beam, in this example including photon 101'. Receptor 201 receives the reflected beam. Computing device 20 directs emitter 101 to emit the beam and measures the time required for cell 201 to detect the reflected beam. The beam travels through tissue at a known constant velocity. The distance from the midpoint between photocells 101 and 201 on centerline 8 to vessel 3, shown as arrow 9, may be calculated from the travel time between emission and detection and the geometrical relationship between photocells 101 and 201.

In one embodiment, one or more lenses may be included to focus, at least partially, the beams emitted by emitter 101 such that the cross-sectional dimensions of the beams remain constant to within a small percentage of their original dimension over the distance of travel of the beams. A collimator may be included to focus beams created by each emitter. Emitter beams may then be correlated to signals produced by detectors to provide additional information about the vessel.

Figure 3:
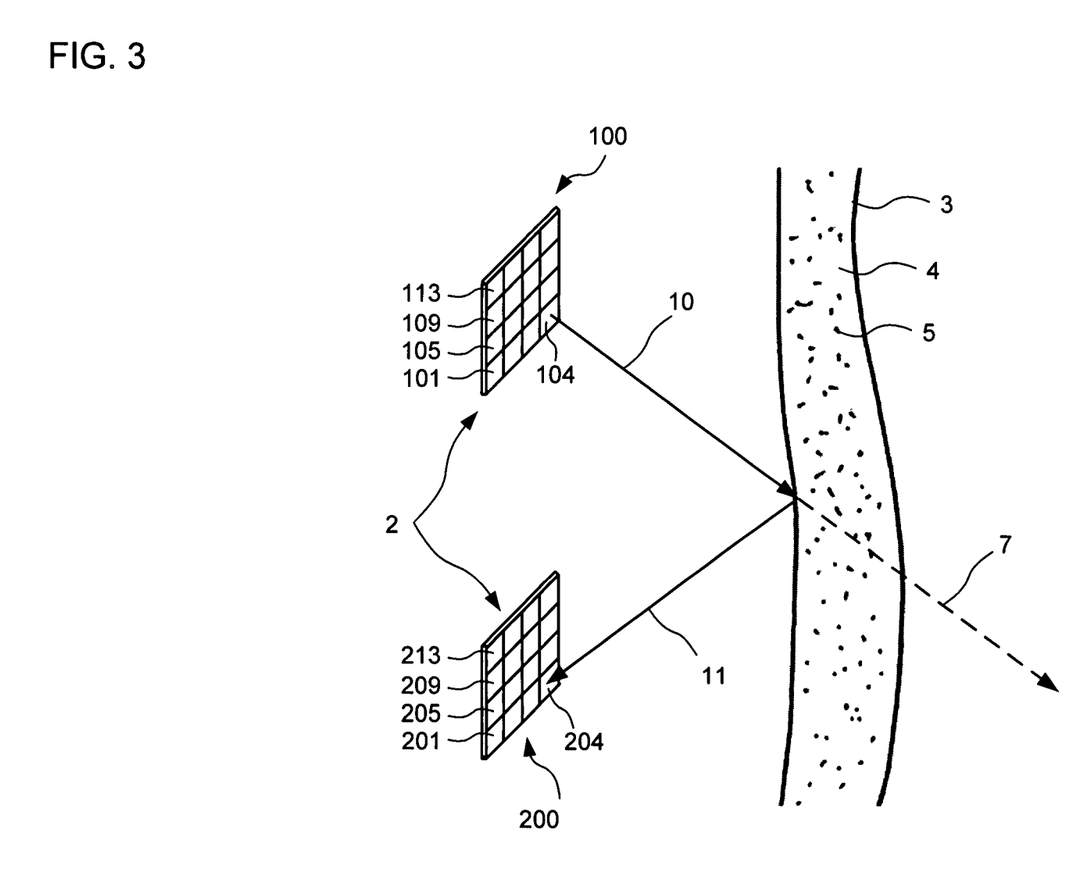
FIG. 3 is a schematic perspective view of a sensor assembly according to one embodiment of the invention and a vessel.
Figure 4:
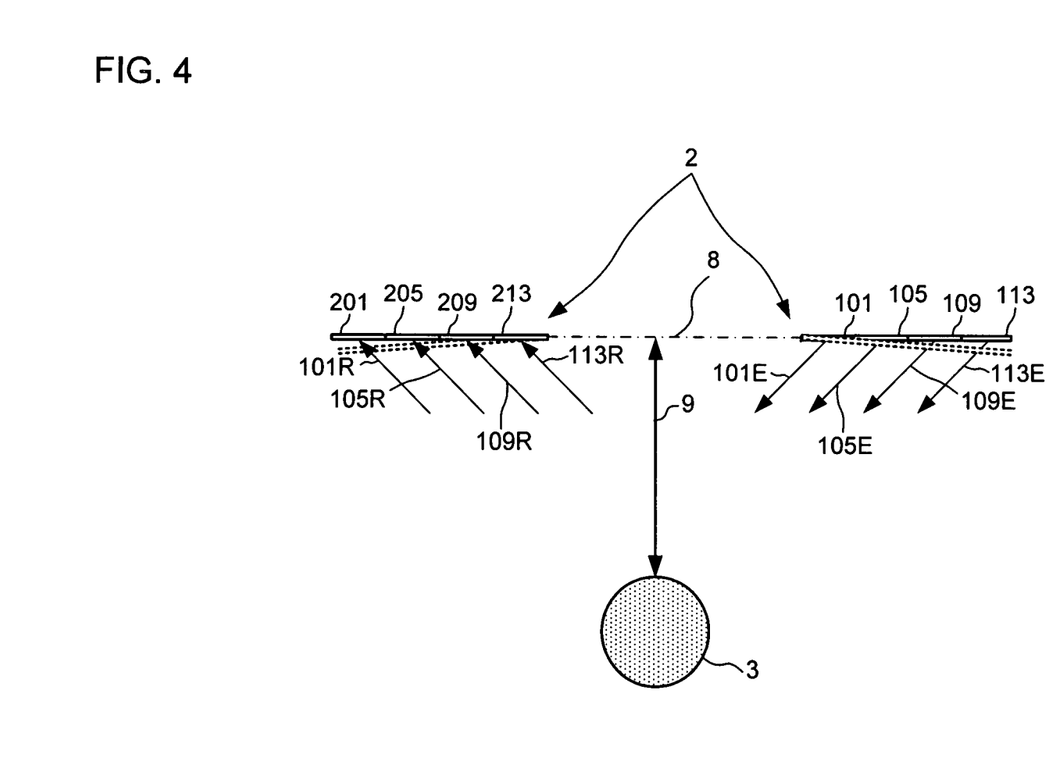
FIG. 4 is a schematic side view of a sensor assembly according to one embodiment of the invention, a vessel, emitted beams, and reflected beams.

FIGS. 3 and 4 illustrate one embodiment of a sensor assembly 2 comprising transmitters and receivers positioned in emitter array 100 and detector array 200, respectively. Emitter array 100 includes sixteen emitters 101-116 disposed in a matrix and may emit sixteen beams as directed by computing device 20. For simplicity, in FIG. 3 only emitted beam 10 from emitter 104 is shown. A portion of beam 10 is reflected from vessel 3 as reflected beam 11. Numeral 7 represents a portion of beam 10 that was not reflected by haemoglobin. Detector array 200 includes sixteen detectors 201-216 disposed in a matrix. Detector array 200 receives the photons in reflected beam 11. More specifically, in this example detector 204 receives photons in reflected beam 11.

Although an exemplary square matrix is shown comprising four rows of four cells each, more or fewer cells may be disposed in sensor assembly 2 depending on the size of the cells, the desired precision of measurements, and the distance between sensor assembly 2 and the target vessel. Enough photons must be emitted to provide a reflected beam suitable for its intended purpose. In another embodiment, each array comprises 25 cells. In yet another embodiment, each array comprises 12 cells. The number of cells in the emitter and detector arrays, and the size of each cell, need not be equal. Additional detectors may be added to the detector array to increase resolution of the mapping of a vessel as is described further below. In one embodiment, the detectors in detector array 200 are square and the length of each side is 1 mm. In another embodiment, each side measures 2.5 mm. The width of an emitted beam may widen slightly with distance. For instance, a 2.5 mm beam may widen to about 3.5 mm when the beam impinges on a vessel located at a distance of 10 cm.

FIG. 4 illustrates a side view of the schematic representation of sensor assembly 2 depicted in FIG. 3. It should be understood that each emitter of emitter array 100 is paired with a corresponding detector of detector array 200. More specifically, emitter 101 is paired with detector 201, emitter 105 is paired with detector 205, emitter 109 is paired with detector 209, and emitter 113 is paired with detector 213. The other emitters and detectors (not shown) are paired in a similar fashion. In one embodiment of the invention, the angle between an emitter and its paired detector is the same for each pair. As shown, emitted beam 113E is directed toward vessel 3 and, if it impinges vessel 3, reflected beam 113R is received by detector 213. For each sensor assembly 2, the angle formed by emitted beam 113E and reflected beam 113R is the same as the angle formed by the emitted and reflected beams of the other emitter cell/detector cell pairs. This angle is referred to herein as the common angle.

It should be understood, however, that a variety of different sensor assemblies 2 may be constructed having different common angles between their respective emitter and detector pairs. For example, the common angle between the cells of emitter array 100 and the paired cells of detector array 200 of FIG. 4 may be 45 degrees. In another sensor assembly 2 configured to penetrate farther into the patient's body, the common angle between the pairs may be 30 degrees. The anatomy of the patient may determine the appropriate sensor assembly 2 to use. For example, when sensing device 1 is implanted subcutaneously in a very thin or very small patient, the distance between sensor assembly 2 and vessel 3 of interest may be small compared to the corresponding distance in a very heavy or very large patient. Therefore, a sensor assembly 2 having a larger common angle between emitters and paired detectors will be appropriate for the thin patient, while a sensor assembly 2 with a smaller common angle will be appropriate for the heavy patient.

It should further be understood that in some embodiments, emitter array 100 and detector array 200 may be mounted in sensing device 1 at an angle relative to one another. In FIG. 4 emitter array 100 and detector array 200 are coplanar (i.e., at an angle of zero relative to one another). As a result of size constraints or desired mounting locations for emitter array 100 and detector array 200, the arrays may be tilted toward one another as shown in dotted lines in the figure.

Figure 5A:
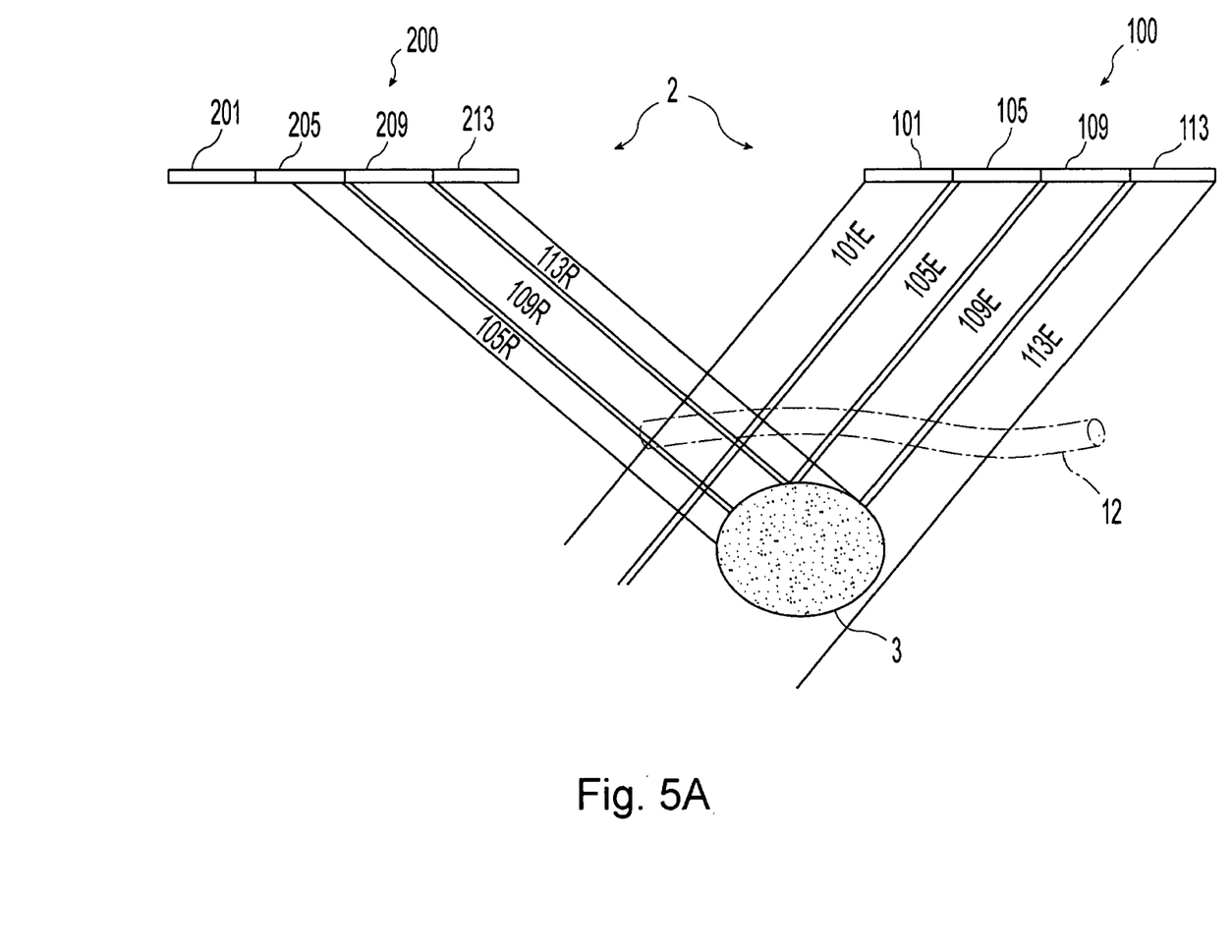
FIGS. 5A, 5B and 5C are schematic side views of a sensor assembly according to one embodiment of the invention, a large vessel, a small vessel, emitted beams, and reflected beams.
Figure 5B:
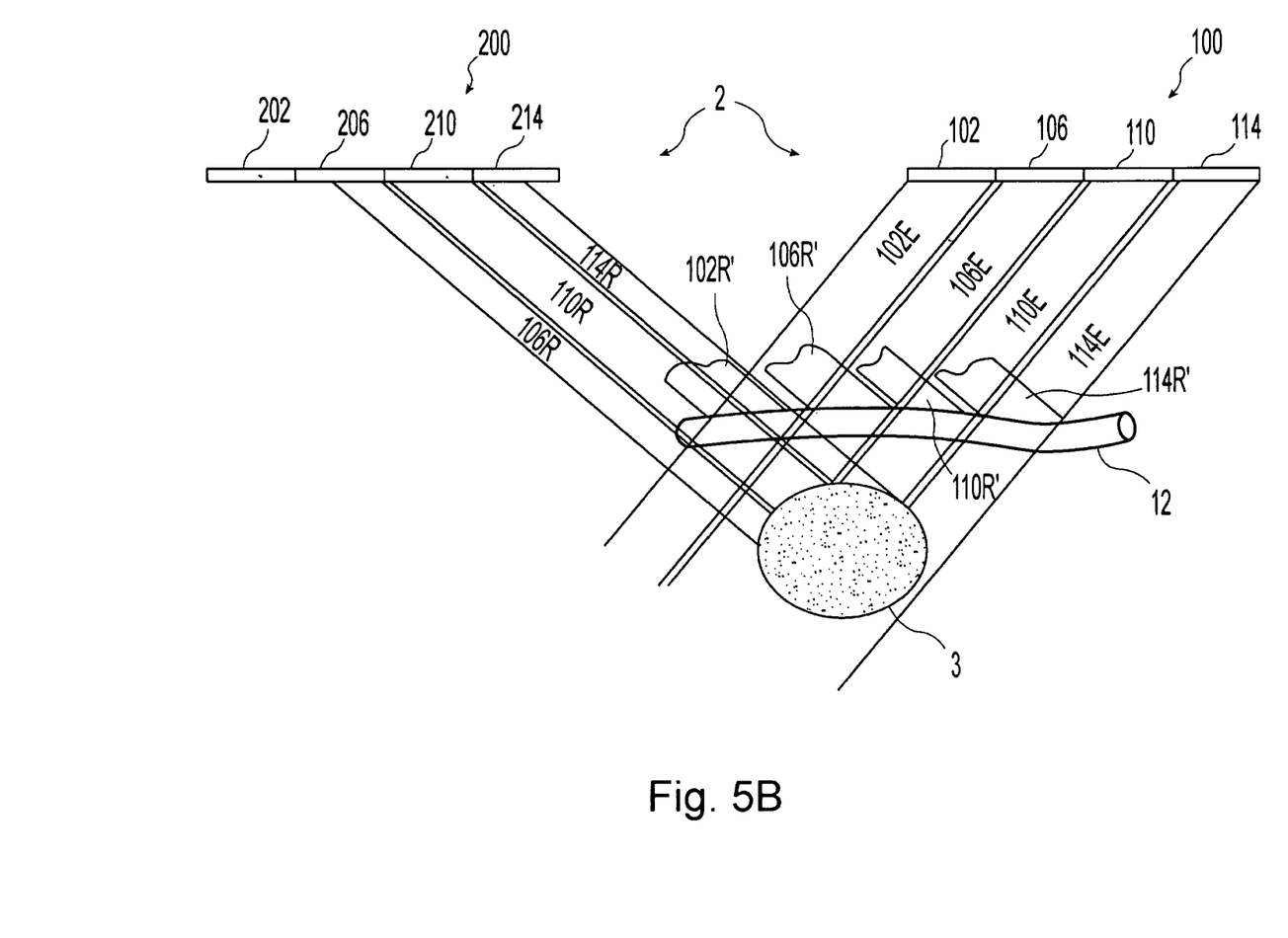
Figure 5C:
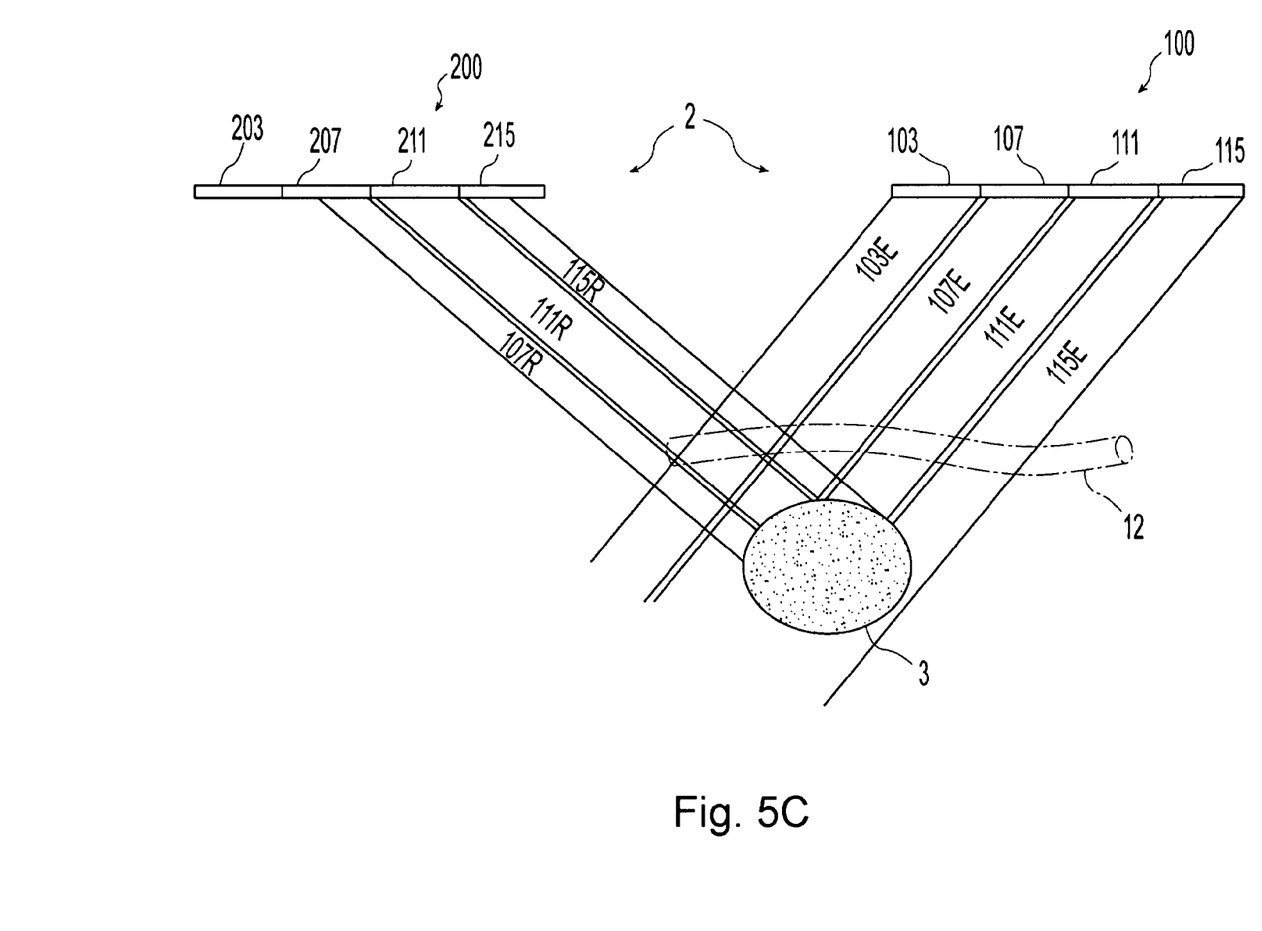

FIGS. 5A-C are schematic representations of sensor assembly 2 depicted in FIG. 4 with the addition of a small vessel 12 oriented perpendicularly to vessel 3. In FIG. 5A, only the cells along the outer edges of emitter array 100 and detector array 200 are shown. Each of the emitter cells 101, 105, 109, 113 emits an IR beam 101E, 105E, 109E, 113E, respectively. Vessel 12 is shown in phantom because it is farther into the figure, and not impinged upon by any of the emitted beams 101E, 105E, 109E, 113E. As shown, emitted beam 101E misses both vessels 3 and 12 entirely. Accordingly, no reflected beam is detected by detector 201. A portion of emitted beam 105E impinges upon vessel 3. A portion of the photons that impinge upon vessel 3 are reflected and detected at detector 205 as reflected beam 105R. All of emitted beam 109E impinges upon vessel 3. The portion of the photons of emitted beam 109E that are reflected by the haemoglobin in vessel 3 are detected at detector 209 as reflected beam 109R. Like emitted beam 101 E, only a portion of emitted beam 113E impinges upon vessel 3 to yield reflected beam 113R at detector 213.

Relative to FIG. 5A, FIG. 5B is a view farther into the page essentially of a plane through the second column of emitters 102, 106, 110, 114 and the second column of detectors 202, 206, 210, 214. In this figure, vessel 12 is shown in solid lines because it is located in the area illuminated by the beams emitted from emitters 102, 106, 110, and 114. When activated, emitter 102 emits emitted beam 102E which misses vessel 3 entirely. A portion of emitted beam 102E, however, impinges upon vessel 12 and a portion of the impinging photons is reflected as reflected beam 102R'. In this example, none of reflected beam 102R' is detected by detector 202 because of the location of vessel 12. As was the case with emitted beam 105E of FIG. 5A, a portion of emitted beam 106E impinges vessel 3. Here, however, another portion of emitted beam 106E impinges vessel 12 before it reaches vessel 3. Some of the photons impinging vessel 12 are reflected as reflected beam 106R', which is not detected by detector 206. Accordingly, the portion of emitted beam 106E that impinges vessel 3 is smaller than the portion of emitted beam 105E that impinged vessel 3 due to the interference of vessel 12. As such, the reflected beam 106R that is detected at detector 206 has less intensity than the reflected beam 105R detected at detector 205. Similarly, the interference of vessel 12 results in reflected beam 110R' and reflected beam 114R' which reduce the number of photons in reflected beams 110R and 114R detected at detectors 210 and 214, respectively.

FIG. 5C is a view even farther into the page essentially of a plane through the third column of emitters 103, 107, 111, 115 and the third column of detectors 203, 207, 211, 213. In FIG. 5C, vessel 12 is again shown in phantom because it does not occupy the area illuminated by emitted beams 103E, 107E, 111E, 115E. As vessel 12 does not interfere with the emitted beams and the location of vessel 3 is the same as shown in FIG. 5A, the path of travel of emitted beams 103E, 107E, 111E, 115E and the characteristics of the resulting reflected beams 107R, 111R, 115R are the same as the corresponding beams described with regard to FIG. 5A.

According to one embodiment of the invention, computing device 20 processes signals received from detector array 200 by filtering, scaling, and conditioning the signals to calculate measurement values corresponding to the intensity, or power, of the beams received by detector array 200. In one embodiment, computing device 20 digitizes analog signals generated by detector array 200. In Tables 1 and 2 below, a value of 1 represents 100% of full power. In other words, a value of 1 equals the power expected to be received by a detector cell if the corresponding emitter cell emits a wave that encounters maximum interference with (and therefore reflection by) a vessel 3 of interest. In an alternative embodiment, an electronic circuit (not shown) is used to filter, scale, and conditioning the signals received from detector array 200 and the output of the electronic circuit is provided to computing device 20 for processing. In another step, computing device 20 evaluates and maps the measurement values to determine the location and diameter of vessel 3, as is further described below.

In one embodiment according to the invention, a full power signal is scaled to equate to a vessel portion having a width of 0.7 centimeters. Each fraction of full power represents linearly a fraction of 0.7 centimeters width. The width, or diameter, of the vessel is calculated by adding measured values in a row or in a column of detector cells, as the case might be. The vessel's diameter is identified when measured values in two or more rows, or columns when values in columns are added, differ by less than 10%. In another embodiment, the vessel's diameter is identified when measured values in two or more rows, or columns, differ by less than 5%.

Table 1 shows a conceptual representation of measured values corresponding to the depiction of vessel 3 shown in FIG. 4. The values indicate that none of the photons in the beams emitted from emitters 101 though 104 were reflected and subsequently detected by the paired detectors 201 through 204 of array 200. More photons were detected by cells in the second row (detectors 205-08) and fourth row (detectors 213-16), and even more by cells in the third row (detectors 209-12). As should be apparent from Table 1, the signals detected in each column of detectors are the same. According to the embodiment disclosed above where a full power signal equates to 0.7 centimeters, the width or diameter of vessel 3 may be computed by multiplying the signal of each detector in a column by 0.7 centimeters, and adding together the resulting products. More specifically, the diameter of vessel 3 in this example is 0.0*0.7+0.8*0.7+1.0*0.7+0.8*0.7, or 1.82 centimeters.

TABLE 1

| Detectors | COL1 | COL2 | COL3 | COL4 |
|---|---|---|---|---|
| 201-04 | 201 | 202 | 203 | 204 |
|  | 0.0 | 0.0 | 0.0 | 0.0 |
| 205-08 | 205 | 206 | 207 | 208 |
|  | 0.8 | 0.8 | 0.8 | 0.8 |
| 209-12 | 209 | 210 | 211 | 212 |
|  | 1.0 | 1.0 | 1.0 | 1.0 |
| 213-16 | 213 | 214 | 215 | 216 |
|  | 0.8 | 0.8 | 0.8 | 0.8 |

Table 2 shows a conceptual representation of processed values similar to Table 1 but corresponding to the depiction of vessels 3 and 12 shown in FIGS. 5A-C. The decreased values in column 2 corresponding to detectors 206, 210, and 214 represent the interference caused by vessel 12 as depicted in FIG. 5B. Values in columns 1, 3 and 4 differ by less than 5% (indeed, as shown they are identical). Thus, computing device 20 may disregard the signals in column 2 and compute the diameter of vessel 2 using the signals in any of columns 1, 3 or 4 in the manner described above.

TABLE 1

| Detectors | COL1 | COL2 | COL3 | COL4 |
|---|---|---|---|---|
| 201-04 | 201 | 202 | 203 | 204 |
|  | 0.0 | 0.0 | 0.0 | 0.0 |
| 205-08 | 205 | 206 | 207 | 208 |
|  | 0.8 | 0.5 | 0.8 | 0.8 |
| 209-12 | 209 | 210 | 211 | 212 |
|  | 1.0 | 0.7 | 1.0 | 1.0 |
| 213-16 | 213 | 214 | 215 | 216 |
|  | 0.8 | 0.5 | 0.8 | 0.8 |

In one embodiment according to the invention, measurement values indicating the presence of vessels having diameters smaller than a predetermined size are deleted, or filtered out, to obtain a clearer representation of vessels of interest. In one embodiment, measurement values corresponding to vessel diameters smaller than 1 centimeter are deleted. In such an embodiment, the vessel of interest is the aorta, which has a known approximate diameter (depending upon the physical characteristics of the patient) that is substantially larger than nearly any other vessel in the vicinity of the mounting location of sensing device 1.

It should be understood that in determining the diameter of a vessel and mapping its location in the manner described above, each of emitters 101-116 are activated individually, in rapid succession. While several emitted beams are shown simultaneously in the various figures, only one beam is emitted at a time to avoid beam overlays and generate a signal un-confounded by such overlays. By emitting one beam and receiving one reflected beam at the paired detector, each signal provides un-confounded information about the vessel. Each signal represents the interference and diffusion experienced by a single beam. In one embodiment of the invention, the beams are emitted individually in a row-by-row scanning fashion, beginning with emitter 101, which is followed sequentially until emitter 116 is activated. In other embodiments, other sequences are followed.

When detectors in an array are scanned, the signal generated by each detector represents the interference and diffusion experienced by each beam. In aggregate, scanning provides information for mapping the location and diameter of a vessel. If blood in a vessel is fully oxygenated, blood will contain more iron and detectors will generate signals representing full power. If blood is not fully oxygenated, detectors will generate signals representing less than full power. However, because scanning occurs quickly, the oxygenation level is constant during each scanning cycle and, therefore, the power differences of the beams received by each detector may be used to map the position and diameter of a vessel regardless of the oxygenation level.

The diameter of the pulmonary artery, which is in the vicinity of the aorta, is similar to the diameter of the aorta. Thus, to identify and measure the diameter of the aorta, sensing device 1 must distinguish between the pulmonary artery and the aorta as both will have a diameter that exceeds the predetermined diameter threshold. Sensing device 1 distinguishes between the two vessels by measuring the oxygen saturation of each, and selecting the vessel with the highest oxygen saturation, which will always be the aorta as the pulmonary artery carries deoxygenated blood from the heat to the lungs.

When making an oxygen saturation measurement, sensing device 1 activates all emitters 101-116 of emitter array 100 simultaneously. First, sensing device 1 computes the position and diameter of a vessel of interest, such as the aorta, by the scanning method already described. Based upon the dimensions of the vessel, the geometrical relation between the emitter and detector arrays and the vessel, and physical characteristics of the emitter and detector arrays, e.g., size of array, width of emitter beams, disposition of emitters and transmitters, sensing device 1 calculates a maximum potential oxygen saturation value according to known photon diffusion equations. Since the physiological characteristics of each patient differ, sensing device 1 may calibrate the maximum potential value for each patient using reference values stored in the memory of computing device 20. Sensing device 1 then simultaneously emits beams from the emitter array, detects reflected beams at the detector array, and converts the reflected beams into power signals. In one embodiment, sensing device 1 aggregates the signals produced from detectors receiving photons reflected by the vessel and divides the aggregate value by the maximum potential value to obtain a saturation ratio which is represents the percentage saturation in the blood flowing through the vessel. In another embodiment, sensing device 1 only activates emitters expected to produce beams that will impinge on the vessel and does not activate emitters whose beams will not impinge on the vessel, to save energy. In another embodiment, sensing device 1 only activates emitters expected to produce beams that will impinge on the vessel and will not impinge on other vessels, to save energy and simplify photon diffusion calculations. In a further embodiment, sensing device 1 may selectively activate pairs of emitters and detectors to minimize the number pairs activated in order to save power.

Under normal operating conditions, sensing device 1 may perform an oxygen saturation measurement once or twice per day. Where an abnormal situation is detected, or when functioning as a pulse detector as described below, sensing device 1 may perform multiple oxygen saturation measurements in a short period of time. Although substantial electrical power is consumed when performing very frequent measurements, the data acquired may be important to the health of the patient.

In one embodiment, sensing device 1 also calculates cardiac pulse. As discussed previously, detectors produce power signals representative of iron content in blood. As the heart pumps oxygenated blood through the aorta, the power signals fluctuate. A plurality of power signals may be obtained in rapid succession to capture the power measurement fluctuation. More specifically, by performing many oxygen saturation measurements (e.g., ten times per second), over a period of time (e.g., fifteen seconds), the saturation measurements will exhibit a pattern or periodicity that represents the beating of the heart. Computing device 20 may determine a curve to fit the saturation measurements, such as a sinusoidal curve, which corresponds directly to the cardiac cycle. Computing device 20 may determine the frequency of peak values of the curve to determine its period. Each period represents a cardiac cycle. By multiplying the number of cardiac cycles in the sample period (e.g., fifteen seconds) by an appropriate factor, computing device 20 may determine pulse rate in terms of cardiac cycles per minute. In one embodiment, computing device 20 stores cardiac pulse values as normal reference values and detects an abnormal or irregular cardiac rhythm by comparing cardiac pulse values to reference values.

In another embodiment of a sensing device 1 according to the invention, sensor assembly 2 and other features of the sensing device 1 are integrated with an implanted cardiac device such as a pacemaker, a Cardiac Resynchronization Therapy (CRT) device, an implantable cardioverter defibrillator (ICD), etc.

2. Computing Device

Computing device 20 comprises a plurality of components. While components are described herein as if they were independent components, the components may be combined in a single device such as an application specific integrated circuit. Computing device 20 includes a processor, a memory, a program, inputs and outputs. The memory may include, but is not limited to, RAM, ROM, EEPROM, flash memory or other memory technology. The processor and memory may be constructed in an integrated circuit. The integrated circuit may include emitter array 100, detector array 200, and communication device 30. Further, computing device 20 may include A/D and/or D/A converters on an integrated circuit. Alternatively, A/D and/or D/A converters may be provided separately.

The program represents computer instructions directing the processor to perform tasks responsive to data. The program resides in the memory. Data, including reference data and measurement data, also resides in the memory. Reference data may be stored in ROM or it may be stored in RAM so that it may be modified over time, either in response to external inputs or in response to characteristics of measurement data collected over time. Protocols for responding to measurement values may also be provided. Protocols may be stored in permanent memory or may be stored in non-permanent memory such as RAM.

Computing device 20 controls sensor assembly 2 and communication device 30 through inputs and outputs. Computing device 20 may control the number, frequency, power level and emission sequence of the plurality of beams emitted by emitters 101-116 to obtain the desired measurements using the least amount of energy.

Figure 6A:
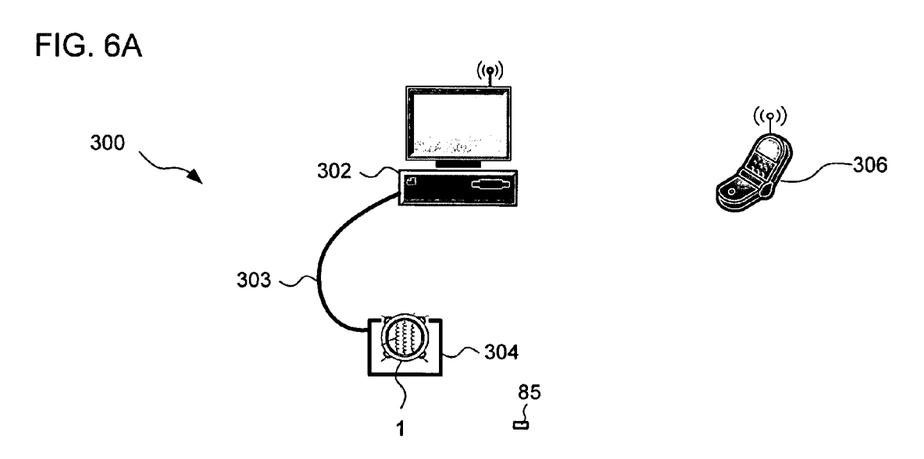
FIGS. 6A and 6B are schematic front and side views, respectively, of a system adapted to communicate with the sensing device of FIG. 1.
Figure 6B:
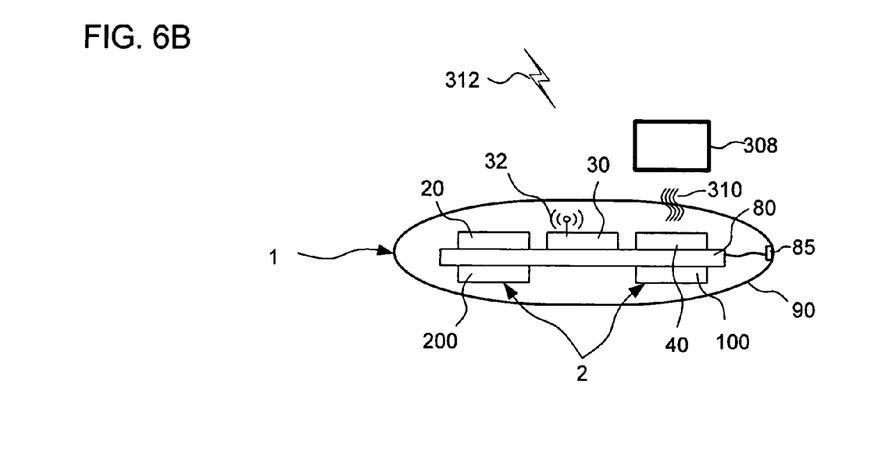

FIG. 6A discloses a system 300 for exchanging information with sensing device 1. System 300 includes sensing device 1 having communication device 30 and, optionally, connector 85. System 300 may also include a computer 302, a docking station 304 operably coupled to computer 302 via cable 303, a telephone 306. In one embodiment of the invention, system 300 transmits and receives communication signals 312 wirelessly to/from sensing device 1 based on processing performed by computing device 20.

Connector 85 is adapted to plug into docking station 304. Sensing device 1 is shown docked on docking station 304. While docked, sensing device 1 may charge energy storage device 40. The docking station is operably coupled to computer 302 to update the programs and reference values stored in the memory of computing device 20 prior to placing sensing device 1 on, or in, the patient. In another embodiment, sensing device 2 is positioned externally to the patient and connector 85 is operationally coupled to an energy source to power sensing device 2 and prevent depletion of energy storage device 40.

In a further embodiment according to the invention, additional sensors and devices may be coupled to sensing device 1 through connector 85. Other sensors and devices may include, without limitation, additional sensor assemblies 2, temperature sensors, pressure sensors, and accelerometers. The other devices may or may not include a computing device. Other devices may also be incorporated with sensing device 1 within housing 90. An integrated sensing device is disclosed in the above-referenced related U.S. Utility Patent Application titled "INTEGRATED HEART MONITORING DEVICE AND METHOD OF USING SAME." The operation of sensing device 1 may be adapted to operate the additional sensors and devices by downloading into the memory of computing device 20 modified programs adapted to operate them. Downloading may occur while computing device 20 is docked in the docking station. Alternatively, new programs may be downloaded wirelessly through computing device 40.

Figure 7:
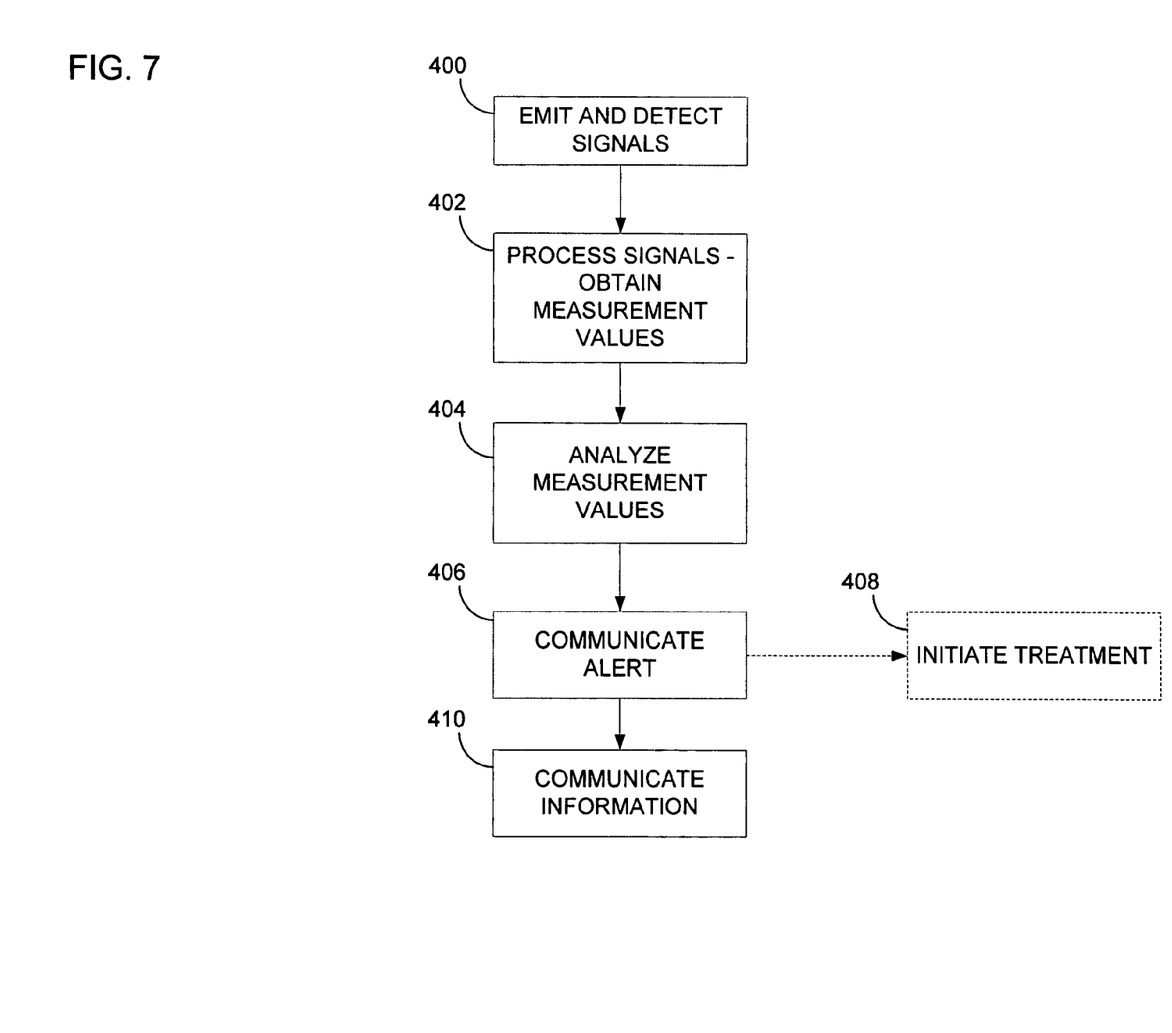
FIG. 7 is a flow-chart of a method according to the invention.

FIG. 7 is a flowchart illustrating one routine of the program performed by computing device 20 according to one embodiment of the invention. At step 400, computing device 20 activates sensor assembly 2 such that all emitters 101-116 emit beams or the emitters sequentially emit individual beams, depending upon the measurement being performed as described above. Step 400 also represents the procedure of generating signals at detectors 201-216 representing reflected beams.

At step 402, computing device 20 processes the signals to obtain measurement values. Processing may involve removing inherent signal noise, converting signals from analog to digital form, optical to digital form, scaling, and otherwise conditioning the detected signals. Alternatively, some processing functions may be performed by circuits such as A/D converters. After processing, measured values may be stored in memory or may be analyzed to determine whether the values should be stored. Steps 400 and 402 may be repeated as necessary to obtain sufficient measurement values to calculate the desired parameters in accordance with the disclosure provided above. Steps 400 and 402 may be performed concurrently.

At step 404, computing device 20 analyzes the measurement values. Analysis may include calculation of parameter data and/or diagnosis. Parameter data refers to calculated values such as vessel diameter and location, oxygen saturation, cardiac rhythm, etc. Diagnosis refers to the comparison of parameter values to reference values to detect an abnormal condition in the patient. Reference data corresponds to a normal condition of the patient. If an abnormal condition is detected, computing device 20 may communicate an alert rather than communicating measurement values as they are collected (consuming unnecessary power) or waiting to transmit measurement values until the memory is full or a predetermined transmission time is reached (exposing the patient to unnecessary danger during the waiting period).

Reference values may include target values and acceptable variation ranges or limits. Parameter values may indicate an abnormality when they fall outside reference target values or ranges. In some embodiments, parameter values may produce a statistic such as, for example, a moving average, and an abnormality would be detected when the parametric statistic differs from a reference statistic by more than an expected amount.

If parameter data differs from expected values by more than a predetermined amount, computing device 20 may initiate a new measurement cycle to verify the parametric data before diagnosing an abnormality. In one embodiment, computing device 20 re-maps the aorta's location and diameter when measured values differ from expected values by more than 10%. In another embodiment, computing device 20 re-maps the aorta's position and diameter when measured values differ from expected values by more than 5%.

One abnormal medical condition is low oxygen saturation. Computing device 20 may be configured to perform an analysis of the measurement values to determine, for example, whether oxygen saturation values are too low. Although the value of "normal" oxygen saturation varies from patient to patient and depends upon the condition of the patient, generally an oxygen saturation measurement of less than 90% is considered low. Another abnormal medical condition is irregular cardiac rhythm which may be detected in the manner described above.

Additional abnormal medical conditions may be detected using values obtained externally or from additional sensors. Additional sensors which may be included in sensing device 1 are disclosed in the above-referenced related U.S. Utility Patent Applications titled "DOPPLER MOTION SENSOR APPARATUS AND METHOD OF USING SAME" and "INTEGRATED HEART MONITORING DEVICE AND METHOD OF USING SAME."

In an embodiment where sensing device 1 includes a Doppler sensor, vessel diameter and location may be used to calculate the velocity of a fluid and the pumping rate. Where the vessel is the aorta, these parameters may be used to calculate and diagnose an abnormal condition relating to cardiac output. Aorta parameters may be combined with systolic and diastolic blood velocity values obtained with the Doppler sensor to calculate systolic and diastolic blood pressure. Other sensors may include an ECG sensor and a temperature sensor.

At step 406, computing device 20 transmits an alert if an abnormal condition is detected, particularly a condition determined to be a serious or dangerous condition according to a prescribed protocol. The alert may be used to actuate an alarm or to alert the patient to take remedial action. A remedial action may be terminating or reducing physical activity. The alert may also provide global positioning (GPS) information to an emergency service. Referring to FIG. 6A, the abnormal condition, when found to be present, may also be displayed on a computer 302 and/or transmitted via communication device 30 (e.g., Nokia modem KNL 1147-V) to a caregiver. The alert may comprise a text message or a code corresponding to the condition. Computing device 20 may also initiate a new measurement cycle and measure on a continuous basis in response to the detection of an abnormal condition.

At step 408, computing device 20 may initiate a treatment. Sensing device 1 may receive, through communication device 30, an external command to perform a treatment in response to the alert. Optionally, based on the protocol, an abnormal condition may also be used to direct a device adapted to provide treatment to deliver such treatment. Treatment may include, for example, an electric shock or a drug delivery.

At step 410, the parameter values or other information are communicated to an external device. Step 410 may be performed concurrently with any of the above steps. The parameter values may be stored in memory and transmitted wirelessly by communication device 30. The communication signal from communication device 30 may be activated on a periodic basis, in response to an abnormal condition, in response to an externally received command, whenever memory usage exceeds a predetermined amount, or whenever the energy storage level is determined to be low, the latter two conditions established to prevent data loss as a result of memory overflow or energy loss. It should also be understood that sensing device 1 may include communication devices in addition to communication device 30. For example, where communication device 30 is a cellular modem, sensing device 1 may also include a backup Bluetooth or RF communication device. Such a backup device may be desirable to provide alternative communication means in situations where cellular modems are unable to transmit information (e.g., due to low available power, poor reception of cellular or other communication signals, poor network coverage, etc.). In such a situation, computing device 20 may activate the backup communication device to transmit information or an alert to an alternate external receiving device.

Step 410 may be performed, for example, once an abnormal condition has been detected so as to update a caregiver on a substantially real-time basis. Step 410 may also be performed at regular intervals, such as once a day, once a week, once a month, etc. Alternatively or in addition to these transmissions, computing device 20 may be programmed to respond to requests for data received by communication device 30 (e.g., from a health care provider) by causing communication device 30 to transmit the requested data or information representing the requested data.

The communication signal may be received by equipment near the patient to alert the patient to the condition, or received remotely (such as over a network) by a healthcare provider, relative, or other predetermined recipient.

3. Communication Device

Referring again to FIG. 6B, a system adapted for transmitting and receiving a communication signal according to one embodiment of the invention is illustrated therein. Communication device 30 is a two-way communication device, e.g. via the cellular telephone system and/or the GPS satellite system. Communication device 30 includes an antenna 32 for transmitting and receiving communication signals. The communication signals, identified by numeral 312, travel wirelessly to and from one of a plurality of optional external communication devices.

An external communication device may be a computer 302 or any electronic device capable of wirelessly receiving a communication signal, such as telephone 306, which is exemplified herein as a cellular phone. Telephone 306 may also be an emergency service switchboard or a hospital or medical center switchboard. By communication signal is meant a signal that has one or more of its characteristics set or changed to encode information in the signal. By way of example, and not limitation, communication signals include acoustic, RF, infrared, other wireless media, and combinations of any of the above. An external communication device may also be a relay unit located externally of the patient's body, e.g. clipped to the patient's belt. The relay unit may include a receiver for receiving the transmissions from communication device 30, and a transmitter for re-transmitting the communication signal to another external communication device. The relay unit may also be stationary and hardwired for connection to the internet or direct connection to a healthcare provider's computer. Likewise, the relay unit may receive a communication signal from a healthcare provider and transmit the signal to communication device 30.

The communication signal from communication device 30 may include a voice message, a text message, and/or measured data. The communication received by communication device 30 may include data, such as updated reference data, or commands. A command may include, for example, instructions to computing device 20 for performing a task such as providing a treatment to the patient, collecting and transmitting additional data, or updating the reference data. Additional embodiments of methods of communicating information according to the invention are disclosed in the above-referenced related U.S. Utility Patent Application titled "METHOD AND SYSTEM FOR MONITORING A HEALTH CONDITION."

4. Energy Storage Device

Referring again to FIGS. 1B, 1C and 6, a system for recharging energy storage device 40 may be provided in one embodiment according to the invention. Computing device 20 receives energy from energy storage device 40. Energy storage device 40 includes an energy storage component such as a battery. Optionally, sensing device 1 may also include an energy coupler for receiving energy from an external source to charge energy storage device 40.

One example of an energy coupler is an electromagnetic device, such as induction coils 308, for receiving external electromagnetic signals 310 and converting such signals into electrical energy for recharging the energy storage component. An external electromagnetic device 308 generates electromagnetic signal 310 which is received and converted into electrical energy by energy storage device 40. Energy storage device 40 may provide a charge signal to computing device 20. Computing device 20 may compare the charge signal to a reference charge signal and initiate a low charge communication signal for alerting the patient and/or healthcare providers. Alternatively, a detector, such as a voltage sensor, may be used to monitor the charge of energy storage device 40 and provide a signal to computing device 20 when the charge falls below a threshold. Electromagnetic device 308 may be placed near sensing device 1 to charge energy storage device 40.

Energy may instead, or additionally, be provided in the form of ultrasonic vibrations. For example, a piezoelectric transducer may be included in sensing device 1. An ultrasonic vibration may be provided externally. The transducer generates electricity when driven by ultrasonic vibrations.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A sensing device for acquiring signals and computing measurements comprising:
   a sensor assembly including a plurality of emitters and a plurality of detectors for generating a plurality of signals;
   a computing device operating the plurality of emitters and detectors and processing the plurality of signals to obtain measurement values;
   an energy storage device configured for powering the computing device and the sensor assembly; and
   a housing enclosing the sensor assembly, the energy storage device, and the computing device,
   the sensing device configured for implantation in a patient wherein the emitters and the detectors are arranged in the housing to face one side of a vessel when implanted, and said processing includes computing, after implantation, a distance from the sensor assembly to the vessel, a diameter of the vessel, and an oxygen saturation value of blood flowing in the vessel.

2. The sensing device of claim 1, wherein the plurality of emitters are arranged in a matrix.

3. The sensing device of claim 2, wherein the plurality of detectors are arranged in a matrix.

4. The sensing device of claim 3, wherein the emitter matrix includes four rows of four emitters and the detector matrix includes four rows of four detectors.

5. The sensing device of claim 1, wherein each detector is operationally paired with a different emitter.

6. The sensing device of claim 1, wherein the number of emitters in the plurality of emitters is different from the number of detectors in the plurality of detectors.

7. The sensing device of claim 1, wherein the sensing device is dimensioned about the same as two stacked quarter dollar coins.

8. The sensing device of claim 1, wherein the sensor assembly and the computing device are integrated in a single piece.

9. The sensing device of claim 1, further including one or more communication devices for transmitting and receiving communication signals.

10. The sensing device of claim 9, wherein the communication device transmits and receives wireless communication signals.

11. The sensing device of claim 9, wherein the communication device includes a connector adapted to operably couple to one or more of a docking station and a second sensing device.

12. The sensing device of claim 9, wherein the sensor assembly, the computing device, and the one or more communication devices are integrated in a single piece.

13. The sensing device of claim 1, wherein the energy storage device includes an energy coupler for receiving energy to recharge the energy storage device.

14. The sensing device of claim 1, said processing further including computing the diameter of the vessel by activating the plurality of emitters to avoid beam overlays, and computing the oxygen saturation value by concurrently activating at least selected emitters from the plurality of emitters.

15. The sensing device of claim 14, the selected emitters corresponding to emitters selected, based on the diameter of the vessel, to emit beams that impinge on the vessel.

16. The sensing device of claim 1, said processing further including computing a plurality of oxygen saturation values and computing a cardiac pulse value based on the plurality of oxygen saturation values.

17. The sensing device of claim 16, said computing device further configured to store a cardiac pulse reference value and to detect an abnormal or irregular cardiac rhythm by comparing the cardiac pulse value to the cardiac pulse reference value.

18. The sensing device of claim 1, the computing device further configured to compute oxygen saturation values at a first frequency during normal operation, and at a second, higher, frequency after detection of an abnormality.

19. A method for acquiring signals and computing measurements comprising:
   providing a sensing device configured for implantation in a patient, the sensing device including
      a plurality of photon emitters and detectors, the emitters emitting beams, the detectors detecting beams and generating a plurality of signals corresponding to the detected beams and
      a computing device for operating the plurality of emitters and detectors,
      an energy storage device configured for powering the computing device and the plurality of photon emitters, and
      a housing enclosing the plurality of photon emitters and detectors, the energy storage device, and the computing device, wherein the emitters and the detectors are arranged in the housing to face one side of a vessel when implanted;
   operating the plurality of emitters and detectors to obtain a plurality of signals;
   processing the plurality of signals, by the sensing device after implantation, to obtain parameter values including a distance from the sensing device to the vessel, a diameter of the vessel, and an oxygen saturation of blood flowing in the vessel.

20. The method of claim 19, wherein the sensing device further includes a communication device, further including the steps of diagnosing a condition using at least one of the parameter values and performing a function in response to the diagnosing step.

21. The method of claim 20, wherein the condition is an abnormal condition.

22. The method of claim 21, wherein the function is communicating an alarm.

23. The method of claim 21, wherein the function is initiating a treatment.

24. The method of claim 23, wherein the treatment is an electric shock.

25. The method of claim 23, wherein the treatment is delivering a drug.

26. The method of claim 20, wherein the function is communicating information on a periodic basis.

27. The method of claim 19, wherein the operating step includes operating emitters and detectors in pairs to obtain measurement values.

28. The method of claim 27, wherein emitter and detector pairs are operated in succession.

29. The method of claim 27, wherein emitter and detector pairs are operated concurrently.

30. The method of claim 27, wherein the operating step includes:
   operating the emitter and detector pairs in succession to obtain a first plurality of signals corresponding to a first parameter value;
   obtaining the first parameter value;
   selecting based on the first parameter value a plurality of emitter and detector pairs; and
   operating the selected emitter and detector pairs concurrently to obtain a second plurality of signals corresponding to a second parameter value.

31. The method of claim 30, wherein the second parameter value is an oxygen saturation value.

32. A device for optically measuring a characteristic of at least one of a blood vessel and blood flowing through the blood vessel, the device including:
   a housing having a first side and a second side;
   a sensor assembly mounted to the housing and including a plurality of emitters for emitting photons through the first side of the housing and a plurality of detectors for receiving at least a portion of the emitted photons though the first side of the housing, each emitter being operationally paired with a separate detector and oriented such that a beam of photons emitted from the emitter that impinges upon a vessel adjacent the sensor assembly will partially reflect toward the paired detector, each detector being configured to produce a signal representing the emitted photons received by the detector; and
   a computing device configured to activate the plurality of emitters and interpret the signals from the detectors to determine the characteristic, the computing device enclosed in the housing and configured to compute
      a diameter of the vessel by activating the plurality of emitters so as to avoid beam overlays,
      a distance from the sensor assembly to the vessel, and
      an oxygen saturation value of the blood flowing in the vessel by concurrently activating at least selected emitters from the plurality of emitters.

33. The device of claim 32, wherein each pair of emitters and detectors is positioned at an angle relative to one another, the angle being the same for all emitter and detector pairs.

34. The device of claim 32, wherein the computing device individually activates each of the plurality of emitters sequentially to determine the diameter of the vessel.

35. The device of claim 32, wherein the computing device activates all of the plurality of emitters simultaneously to determine the oxygen saturation of the blood.

36. The device of claim 32, the selected emitters corresponding to emitters selected, based on the diameter of the vessel, to emit beams that impinge on the vessel.

37. The device of claim 36, further configured to compute a plurality of oxygen saturation values and to compute a cardiac pulse value based on the plurality of oxygen saturation values.

38. The device of claim 32, further configured to store a cardiac pulse reference value and to detect an abnormal or irregular cardiac rhythm by comparing the cardiac pulse value to the cardiac pulse reference value.

\* \* \* \* \*